United States Patent [19]

Chum et al.

[11] Patent Number: 4,617,090
[45] Date of Patent: Oct. 14, 1986

[54] PROCESS FOR PRODUCING PERACIDS FROM ALIPHATIC HYDROXY CARBOXYLIC ACIDS

[75] Inventors: Helena L. Chum, Arvada; Matthew A. Ratcliff; Peter D. Palasz, both of Lakewood, all of Colo.

[73] Assignee: The United States of America as represented by the United States Department of Energy, Washington, D.C.

[21] Appl. No.: 684,099

[22] Filed: Dec. 20, 1984

[51] Int. Cl.[4] ............................................... D21C 9/16
[52] U.S. Cl. ................................ 162/16; 260/502 A; 568/484; 162/76; 204/79
[58] Field of Search ...................... 260/502 A; 204/79; 162/16, 76; 568/484

[56] References Cited

U.S. PATENT DOCUMENTS

| | | | |
|---|---|---|---|
| 2,804,473 | 8/1957 | Phillips et al. | 564/298 |
| 3,502,715 | 3/1970 | Inoue et al. | 260/502 A |
| 4,137,256 | 1/1979 | Slattery et al. | 260/502 A |
| 4,461,691 | 7/1984 | Frank | 204/79 |

OTHER PUBLICATIONS

Johnson et al, *Chemical Abstracts*, vol. 48, No. 1783c, 1954.
Rigby, *Chemical Abstracts*, vol. 44, No. 1020e, 1950.
Rigby, *Chemical Abstracts*, vol. 45, No. 1021i, 1951.
Everett et al, *Chemical Abstracts*, vol. 40, No. 547[4], 1946.
Alen et al, *Chemical Abstracts*, vol. 93, No. 241415q, 1980.
Stieber et al, *Chemical Abstracts*, vol. 92, No. 39986a, 1980.
Weissermel et al, *Industrial Organic Chemistry*, pp. 152–153, (1978).
Baizer et al, Ed., *Organic Electrochemistry*, pp. 435–462, (1983).
Allison, *Chemical Abstracts*, vol. 95, No. 171305u, (1981).

*Primary Examiner*—Natalie Trousof
*Assistant Examiner*—Bruce D. Gray
*Attorney, Agent, or Firm*—Kenneth L. Richardson; James W. Weinberger; Judson R. Hightower

[57] ABSTRACT

A process for producing peracids from lactic acid-containing solutions derived from biomass processing systems comprising: adjusting the pH of the solution to about 8–9 and removing alkaline residue fractions therefrom to form a solution comprised substantially of lower aliphatic hydroxy acids; oxidizing the solution to produce volatile lower aliphatic aldehydes; removing said aldehydes as they are generated; and converting said aldehydes to peracids.

6 Claims, 2 Drawing Figures

PROCESS FOR PRODUCING PERACIDS FROM ALIPHATIC HYDROXY CARBOXYLIC ACIDS

CONTRACTUAL ORIGIN OF THE INVENTION

The United States Government has rights in this invention under Contract No. DE-AC02-83CH10093 between the U.S. Department of Energy and the Solar Energy Research Institute, a Division of the Midwest Research Institute.

BACKGROUND OF THE INVENTION

1. Field of the Invention

The present invention relates to processes for converting hydroxy carboxylic acids to useful products and, more particularly, to processes for decarboxylating carboxylic acids to produce peracids and other useful products. Specifically, the present invention relates to a process for decarboxylating polyfunctional carboxylic acids derived from biomass processing systems in order to produce useful products.

2. Description of the Prior Art

There are a wide variety of biomass processing systems which produce waste streams containing substantial portions of lactic acid and other hydroxy acids. Examples of such biomass processing systems include the pulp and paper industry utilizing alkaline chemical pulping methods such as the kraft and soda pulping processes. Cheese whey production also contains substantial amounts of lactic acid. During, for example, alkaline chemical pulping processes, the unavoidable degradation of polysaccharides leads to the production of saccharinic and lactic acids in substantial amounts, approximately 22% of the weight of the initial wood. In addition, saturated aliphatic carboxylic acids such as formic acid and acetic acid are also components of the liquor. These acids, as sodium salts, together with the dissolved lignin compose the spent liquor. Present day wood pulping processes burn these chemicals to recover the salts for reuse in the pulping process. The component having the largest fuel value of the spent liquor is the alkali lignin. Therefore, it would be highly desirable to find some other high value use for the hydroxy acids produced by these processes.

U.S. Pat. No. 4,303,488 describes a process for photoelectrochemically converting saturated carboxylic acids, such as acetic and propionic acids, to their corresponding alkanes, methane and ethane respectively. These resultant alkanes can be useful as low value gaseous fuels. Carboxylic acids (RCOOH) can also be electrolytically oxidized to alkanes (RR) or mixtures of alkanes, alkenes, esters and alcohols as exemplified in the text entitled *Organic Electrochemistry*, edited by M. M. Baizer and H. Lund, pages 435-462, 1985. The electrochemical behavior is a function of the electrode material, current density, solvent system, temperature and pressure. The behavior of polyfunctional carboxylic acids is a complex function of the above parameters and of the susceptibility of the functional group (other than the carboxylate) to the anodic potential.

It has long been known that lower aliphatic peracids can be produced from corresponding aldehydes. Examples of such production are illustrated in U.S. Pat. No. 2,804,473, issued Aug. 27, 1967, and in a text entitled, *Industrial Organic Chemistry* by Klaus Weissermel and Hans-Jurgen Arpe, pages 152 and 153, 1978. Alternative schemes for production of peracids involve the reaction of the carboxylic acids with hydrogen such as described in U.S. Pat. No. 4,101,570 issued in 1978. A further route to peracids is to oxidize volatile aldehydes to the corresponding carboxylic acids and then react these acids with hydrogen peroxide to produce lower aliphatic peracids. Peracids are very useful in the wood pulping industry as bleaching agents. Therefore, it would be highly desirable to produce peracids for use or reuse by the wood pulp industry.

SUMMARY OF THE INVENTION

Accordingly, it is one object of the present invention to provide a process for converting lactic acid-containing solutions derived from biomass processing systems to useful products.

It is another object of the present invention to provide a process for converting hydroxy acids present in side streams derived from biomass processing systems to peracids useful in pulp chlorine-free bleaching schemes.

It is yet another object of the present invention to provide a process for decarboxylating polyfunctional carboxylic acids to produce aldehydes which may then be subsequently converted to other useful end products such as peracids.

Additional objects, advantages and novel features of the present invention shall be set forth in part in the description that follows, and in part will become apparent to those skilled in the art upon examination of the foregoing or may be learned by the practice of the invention. The objects and advantages may be realized and attained by means of the instrumentalites and in combinations particularly pointed out in the appended claims.

To achieve the foregoing and other objects and in accordance with the purpose of the present invention, as embodied and broadly described herein, a process is disclosed for producing peracids from lactic acid-containing solutions derived from biomass processing systems. The process includes adjusting the pH of the solution to about 8-9 and removing alkaline residue fractions therefrom to form a solution comprised substantially of lower aliphatic hydroxy acids. This solution is then oxidized to produce volatile lower aliphatic aldehydes. The aldehydes are removed as they are generated and then converted to peracids by any one of a number of schemes. In one preferred embodiment of the invention, the solution is cooled to enhance the amount of lactic acid therein, the cooking occurring immediately before or after the removal of the alkaline residue fraction.

BRIEF DESCRIPTION OF THE DRAWINGS

The accompanying drawings which are incorporated in and form a part of the specification illustrate preferred embodiments of the present invention, and together with the description, serve to explain the principles of the invention. In the drawings.

DETAILED DESCRIPTION OF THE PREFERRED EMBODIMENTS

Figure 1:
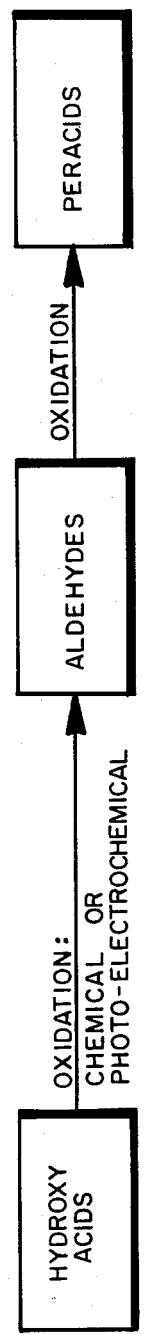
FIG. 1 is a brief flow diagram showing the general process of the present invention.

As previously indicated, hydroxy acids are produced in substantial amounts by a variety of biomass processing systems. Referring to FIG. 1, these hydroxy acids may be oxidized by an oxidizing means for direct chemical, electrochemical or photoelectrochemical oxidation to form their corresponding aldehydes. The aldehydes can then be converted using a variety of techniques to their corresponding peracids which are useful chlorine-free bleaching agents for the pulp and paper industry.

The manner of obtaining the hydroxy acid solution is discussed in greater detail below. However, once this solution containing a variety of polyfunctional carboxylic acids is obtained, the acids may be oxidized to their corresponding aldehydes by photoelectrochemical oxidation techniques. In one preferred form of the invention, the hydroxy acid solution, at a pH of about 3–4, is admixed with a powdered semiconductor electrode to form a slurry. A preferred semiconductor electrode material includes doped platinized n-TiO$_2$ as anatase. Other semiconductor electrode material choices include mixtures of doped anatase/rutile in platinized form, tungsten trioxide (n-WO$_3$), $\alpha$-Fe$_2$O$_3$, and other insoluble semiconductor materials having bandgaps equal to or higher than the ferric oxide.

The slurry containing the hydroxy acids and the semiconductor electrode material is then irradiated at a temperature of about 50°–90° C. The preferred and most economical source of such irradiation is solar although artificial irradiation can be utilized. Irradiation of the slurry causes a photoelectrochemical reaction at the site of the semiconductor material resulting in decarboxylation of the carboxylic acids and production of CO$_2$ and corresponding aldehydes.

Typical hydroxy acids produced in biomass processing systems include lactic acid, saccharinic acids, hydroxybutanoic acids and glycolic acids. Typically, the aldehydes produced from such acids include acetaldehyde from lactic acid, formaldehyde, and propanaldehyde. These are the principal acids and aldehydes envisioned by the process of the present invention. However, other organic acids and corresponding aldehydes may also be present and formed.

The aldehydes formed from such photoelectrochemical oxidation are volatile and gaseous in nature. Therefore, in order to prevent further oxidation of the aldehydes, the aldehydes are swept away and removed as soon as they are formed. These aldehydes are then subsequently converted to their corresponding peracids by any number of techniques. Some of the preferred techniques are discussed in greater detail below.

The hydroxy acids may also be converted to their corresponding aldehydes by direct chemical oxidation. In this instance, the oxidation occurs in an aqueous solution at the same temperature range of approximately 50°–90° C. The preferred oxidants to be used must have several properties. They must convert $\alpha$-hydroxy acids to aldehydes in high yields, be low in cost, use water as the solvent for the reaction, be capable of electrochemical regeneration (e.g., NaIO$_4$), be capable of being disposed of by burning if it is sufficiently inexpensive so as not to warrant electrochemical regeneration, must not interfere with the recovery of inorganic compounds, and must be compatible with facilities and chemicals already used in the biomass processing system such as with pulping (e.g., Na$_2$S$_2$O$_8$). While there are any number of potential oxidants which may be utilized in the present invention, some of the more preferred oxidants include NaIO$_4$, either alone under acid conditions or with an OsO$_4$ catalyst under basic conditions; Na$_2$S$_2$O$_8$ with an Ag$^+$ catalyst or other transition metal ion catalysts; Ce(SO$_4$)$_2$; K$_2$Cr$_2$O$_7$ or Na$_2$Cr$_2$O$_7$ preferably with a Mn(II) catalyst; Ca(OCl)$_2$ preferrably with H$_2$SO$_4$ or HAc and with or without Pb ion catalyst; NaOCl under the same conditions as Ca(OCl)$_2$; NaOBr; NaBiO$_3$ preferably in an H$_3$PO$_4$ medium; and basic KMnO$_4$ or NaMnO$_4$.

Once the gaseous aldehydes are formed, they are immediately swept away so as to prevent further oxidation. It is important that only sufficient oxidant be added to the hydroxy acid solution so as to permit initial oxidation to the aldehyde. Otherwise, if an overabundance of oxidant is added, the aldehydes may undergo additional oxidation to carboxylic acids. In preferred form, the aldehydes are swept away, in either nitrogen or air. Once the aldehydes are swept away they are gathered and then subjected to one of several processes in preferred form, to produce their corresponding peracids. This can be seen particularly in the latter part of FIG. 2 where the three preferred choices are illustrated.

The first manner of converting the gaseous aldehydes to peracids is a vapor phase reaction such as described in U.S. Pat. No. 4,137,256 issued in 1979. In this particular technique, the gaseous aldehydes are reacted with oxygen to form corresponding peracids. In a second alternate form, the gaseous aldehydes may be extracted in a solvent. This extraction may take place in an extraction tower, and the solvent may be any appropriate solvent not miscible with water. A preferred example of such a solvent is ethyl acetae. Once the aldehydes are extracted into the solvent, they are then oxidized by oxygen followed by thermal cracking of the reactive intermediates which lead to the formation of the appropriate peracids.

Figure 2:
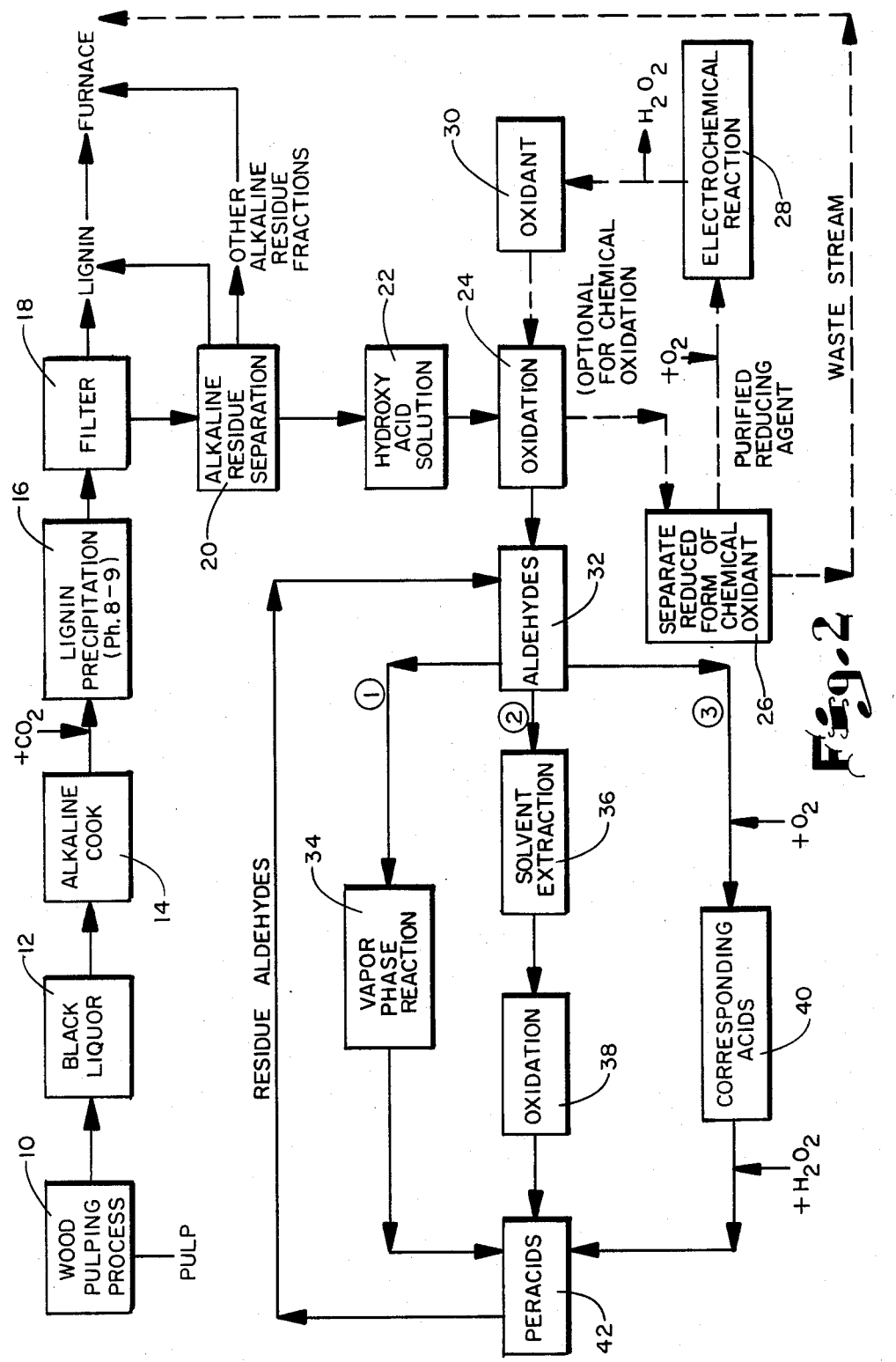
FIG. 2 is a more detailed flow diagram illustrating one embodiment of the process of the present invention as it applies to the wood pulping industry.

The third main route to convert the aldehydes to their corresponding peracids is illustrated by route 3 of FIG. 2. In this particular instance, the gaseous aldehydes are reacted with oxygen to form their corresponding acids, and these acids are then reacted with hydrogen peroxide(H$_2$O$_2$) to form the corresponding peracids. It should be noted that all three routes to convert the aldehydes to peracids are known to the art and can be found in any number of references. Moreover, any other known processes for converting aldehydes to peracids may be utilized with the present invention so long as the compounds utilized therewith do not interfere with or react negatively to any of the other constituents present in the overall process of the present invention.

Referring specifically, now, to FIG. 2, a more detailed flow diagram is shown wherein the process of the present invention is adapted for use with lactic acid-containing solutions derived from a wood pulp process. A standard wood pulp process 10 produces wood pulp as well as a liquid stream termed black liquor 12. The general object of a chemical wood pulping technique is to separate the wood fibers from each other with minimum mechanical damage. This can be accomplished by the action of suitable chemicals that remove the more soluble cementing materials, largely lignin and hemicelluloses. This leaves behind a fibrous mass, the pulp.

TABLE I

Products Obtained on Kraft Pulping. Approximate values in kg/ton of pulp.

| Component | Pine | Birch |
| --- | --- | --- |
| Lignin | 510 | 340 |
| Hydroxy Acids | 310 | 240 |
| Glycolic | 10 | 15 |

TABLE I-continued

Products Obtained on Kraft Pulping. Approximate values in kg/ton of pulp.

| Component | Pine | Birch |
|---|---|---|
| Lactic | 45 | 45 |
| 2-Hydroxybutanoic | 15 | 65 |
| 2, 5-Dihydroxypentanoic | 10 | 10 |
| Xyloisosaccharinic | 15 | 45 |
| Glucoisosaccharinic | 160 | 35 |
| Formic acid | 70 | 50 |
| Acetic acid | 50 | 120 |
| Resin and/or fatty acids | 75 | 50 |
| Turpentine | 10 | — |
| Miscellaneous (mainly neutral substances) | 100 | 85 |

The black liquor 12 includes a number of different chemical constituents including a large portion of saccharinic acids and lactic acids as well as other hydroxy acids. Examples of typical compositions of black liquor derived from both a softwood and a hardwood species are shown in Table I above. The black liquor is generally highly alkaline. Since the present invention enables lactic acid to be ultimately converted to peracetic acid which is a highly desirable chlorine-free bleaching agent for use in wood pulping processes, it is clearly desirable to increase the amount of lactic acid as much as possible. Thus, the black liquor is preferably subjected to an alkaline cooking step 14. The alkaline cook preferably takes place at 150°-200° C. for approximately 2-4 hours in the presence of oxygen during which time lactic acid is produced by base-promoted rearrangement of the acids. It is important to note that the alkaline cook step 14, however, is not essential to the present invention although it is desirable since it increases lactic acid yield. Moreover, if the process begins with a lactic acid solution from cheese whey processing, such a cooking step 14 is not needed. Finally, the alkaline cook can also occur after the alkaline residue separation step 20 discussed below.

Subsequent (in the most preferred embodiment) to the alkaline cook, the solution is acidified preferably by bubbling $CO_2$, a pH adjusting means, through the solution to reach a pH of about 8-9 and to precipitate alkaline lignin at step 16. The lignin is then filtered at 18, and the residual solution is directed to an alkaline residue separation process 20. The lignin precipitate is burned in accordance with standard wood pulping processes to provide heat for the wood pulping as well as to recover inorganic chemicals used in the wood pulping process.

At the alkaline residue separation step 20, additional alkaline lignin as well as other alkaline residue fractions are filtered from the solution. This may be achieved in several ways. In preferred form, the solution is maintained at a basic pH, and the alkaline residue fractions are separated therefrom using standard and well known ultrafiltration techniques or membrane separation processes. In an alternate form, the solution may first be acidified to a pH of approximately 3-4 by the addition of $H_2SO_4$ or the like. This acidification causes alkaline lignin and other alkaline residue fractions to precipitate further after which these solutions are then filtered to remove the precipitated materials.

The resulting solution 22 is highly concentrated in hydroxy acids and in particular lactic acid. These hydroxy acids are then converted to their corresponding aldehydes by an oxidation step 24. A key to the process of the present invention is that the aldehydes are produced in gaseous form. The oxidation steps available for converting the hydroxy acids to their volatile aldehydes are discussed in greater detail above. In the case of the process illustrated in FIG. 2, when the chemical oxidation technique is utilized, a separate recycling phase may be used to recycle the oxidants used in step 24. More specifically, of the previously disclosed chemical oxidants, $NaIO_4$ is preferred for the process of FIG. 2. In this instance, it is the periodate ion($IO_4^-$) which is the oxidant. The periodate ion is reduced during the oxidation step 24 to iodate ion ($IO_3^-$). This all takes place in an aqueous environment. The $IO_3^-$ ion appears in step 26 and is recycled by oxidizing it in an electrochemical reaction 28 so as to regenerate the $IO_4^-$ ion while generating $H_2O_2$. The regenerated periodate ion is then recycled at step 30 for use in the oxidation step 24. An alternate method for recycling the iodate ion is to subject it to methanol and cool down so as to precipitate $NaIO_3$ which may then be separated from solution and converted to $IO_4^-$ by oxidation step 28 while oxygen is converted to $H_2O_2$ (other reductions can be used as well). Other recycling processes are envisioned for use in the present invention which are within the skill of the art.

As the hydroxy acids are oxidized in step 24, volatile gaseous aldehydes are generated at 32. These aldehydes are swept away as soon as they are generated to prevent further oxidation to their corresponding carboxylic acids. The aldehydes are then preferably converted to their corresponding peracids through one of three processes as previously described. The first process 34 is a vapor phase reaction. The second alternate process 36 is a solvent extraction followed by air oxidation 38. The third alternate process is converting the aldehydes at step 40 to their corresponding acids by subjecting the aldehydes to oxygen and then converting these acids to peracids by reacting them with hydrogen peroxide. The results at 42 are a mixture of peracids based upon the hydroxy acid mixture at step 22. Given the fact that the majority of the solution at step 22 is comprised of lactic acid, the major aldehyde formed is acetaldehyde which is converted to peracetic acid at 42.

The following examples are provided by way of illustration only and are not to be deemed to be limiting in any manner.

EXAMPLES I-IV

Table II below discloses some figures for Examples I-IV for photoelectrochemical conversion of hydroxy acids to aldehydes.

TABLE II

| | | LACTIC ACID PHOTOELECTROCHEMICAL REACTIONS | | | |
|---|---|---|---|---|---|
| NO.[1] | ACID CONC. | SEMICONDUCTOR | ILLUM. TIME (HRS.) | NOMINAL ILLUM. POWER (W.) | % CONVERSION TO ALDEHYDES |
| I | 10 mls. 0.5 M | DOPED $Pt/TiO_2$ 20 mg | 3 | 1960 | 11.8 |
| II | 10 mls. | SPUTTERED $Pt/TiO_2$ | 4 | 2030 | 2 |

TABLE II-continued

LACTIC ACID PHOTOELECTROCHEMICAL REACTIONS

| NO.[1] | ACID CONC. | SEMICONDUCTOR | ILLUM. TIME (HRS.) | NOMINAL ILLUM. POWER (W.) | % CONVERSION TO ALDEHYDES |
|---|---|---|---|---|---|
| III | 0.5 M 10 mls. 0.5 M | 56 mg DOPED $Pt/TiO_2$ 58 mg | 3 | 1960 | 26.6 |
| IV | 10 mls. 0.5 M | DOPED $Pt/TiO_2$ 55 mg .2 m mol $NaIO_4$ | 4 | 1960 | 38.2 |

[1]pH = 4; Temp = 65° C.

For each of the above Examples I–IV, loadings of 5 mg/ml of powdered catalyst with acid concentrations of up to 1.0M were utilized. The decarboxylation rates of 0.25 m moles/hr. to 0.5 m moles/hr. were observed for illuminations in the nominal range of 1000 to 2000 W with a solar simulator. The preferred conditions for the Examples I–IV comprised semiconductor electrodes (doped and platinized) in the presence of inorganic electrochemical mediators such as periodate($IO_4^-$) ions as in Example IV. These ions apparently increased the decarboxylation rate to 0.7–1.0 m. moles/hr. If the Examples III and IV are compared, the conversions per hour are 8.8% and 10% respectively. Based on the percent of conversion, Example IV provided the best conditions.

EXAMPLES V–XV

These Examples V–XV are additional photoelectrochemical conversions of lactic acid to the corresponding acetaldehyde using a variety of different semiconductor materials. As can be seen from Table III, Examples XII–XIV provided the best conversion rate (about 8% per hour) without inorganic mediators, which are in agreement with Example III of Table II. The testing conditions for these Examples V–XV were the same as those for I–IV.

TABLE III

LACTIC ACID PHOTOELECTROCHEMICAL REACTIONS

| NO. | ACID CONC. | SEMICONDUCTOR | ILLUM. TIME (HRS.) | NOMINAL ILLUM. POWER (W.) | % CONVERSION TO ALDEHYDES |
|---|---|---|---|---|---|
| V | 15 mls 1.0 M | $Fe_2O_3$ 175 mg/15 ml | 8.4 | 2100 | No Aldehyde |
| VI | 15 mls 0.5 M | $Pt/Fe_2O_3$ 150 mg/15 ml | 10 | 1900 | 2.1 |
| VII | 15 mls 0.5 M | Doped $Pt/TiO_2$ 83 mg/15 ml | 4 | 2300 | 17.6 |
| VIII | 14 mls >0.5 M | Doped $Pt/TiO_2$ 67 mg/15 ml | 3 | 1960 | 20.0 |
| IX | 11 mls 0.5 M | Doped $Pt/TiO_2$ 60 mg/11 ml | 4 | 940 | 17.1 |
| X | 10 mls 0.25 M | Doped $Pt/TiO_2$ 55 mg/10 ml | 10 | 1510 | 66.0 |
| XI | 10 mls 0.5 M | $WO_3$ 100 mg/10 ml $PtCl_6$ in soln | 5.75 | 1940 | 2.2 |
| XII | 10 mls 0.5 M | 5.3% $Pt/TiO_2$ 56 mg/10 ml | 3 | 1940 | 23.0 |
| XIII | 10 mls 0.5 M | Doped $Pt/TiO_2$ 54 mg/10 ml | 3 | 1540 | 25.2 |
| XIV | 10 mls 0.5 M | Doped $Pt/TiO_2$ 54 mg/10 ml | 3 | 1960 | 26.4 |
| XV | 9.6 mls 0.5 M | Doped $TiO_2$ 58 mg | 3 | 1970 | 1 |

In these Examples direct chemical oxidations of the hydroxy acids to their corresponding aldehydes were performed. These tests were performed at a temperature of approximately 50°–90° C. The oxidants indicated in Tables IV and V below were added continuously in a drop-wise fashion to the hydroxy acid solution to prevent further oxidation of the aldehydes to carboxylic acids. As the aldehydes were generated, they were removed by a nitrogen or air gas flow. The aldehydes are measured as their corresponding 2,4-dinitrophenylhydrazones (DNPH).

TABLE IV

Results from the Dropwise Addition of Sodium Periodate to Lactic Acid

| Example No. (Lactic Acid) | % of Products Based on Initial Acid[a] | | | |
|---|---|---|---|---|
| | DNPH | $CO_2$ | Unreacted | Total Mass Balance |
| XVI | 73 | 69 | 30 | 103 |
| XVII | 91 | 80 | 26 | 117 |
| XVIII | 90 | 83 | 20 | 110 |

[a]Trace amounts of formic and acedic acids were also formed.

TABLE V
Results for the Dropwise Addition of Periodate to Hydroxy Acids

| Example NO. | Acid | (g) | DNPH # | CO$_2$ mmoles | Unreacted | Formic |
|---|---|---|---|---|---|---|
| XIX | Glucometa-saccharinic 603 | 0.5032 (3.11 mmol) | 0.38 | 3.05 | 0.50 | 3.69 |
| XX | Southern Yellow Pine 606 | 0.9950 | 0.70 | 3.83 | b | 3.17 |
| XXI | Aspen | 0.9491 | 0.99 | 7.10 | b | 3.09 |

DNPH based on acetaldehyde molecular weight.
$^b$Nearly complete oxidation of the hydroxy acids with only traces of glycolic acid remaining in the sample.

The amount of volatile acetaldehydes formed from lactic acid increased from about 50% to 90% on going from batch to drop-wise addition of oxidant. Unfortunately, there was no significant increase in the amount of volatile aldehydes formed from glucoisosaccharinic acid. The remainder of the experimental conditions for these Examples XIX–XXIV are described previously in the direct oxidation process description.

Examples XXII–XXVIII

Table VI illustrates the results for Examples XXII–XXVIII. In these Examples, a series of different oxidants were used to directly oxidize some hydroxy acids. The purpose of these Examples XXII–XXVIII was to investigate the possibility of using oxidants other than periodate to obtain aldehydes from the hydroxy acids. The reactions were performed under similar conditions as in Examples XVI–XXI in that the oxidant was added drop-wise to the hydroxy acids, and the reactants were kept at a temperature of approximately 70°–80° C.

TABLE VI
Experimental results using different oxidants on α-hydroxy acids.

| Examples No. | Substrate | Oxidant | % Conversions DNPH | CO$_2$ |
|---|---|---|---|---|
| XXII | Lactic Acid | K$_2$Cr$_2$O$_7$ | 4.0 | 58.0 |
| XXIII | Lactic Acid | NaOCl | 11.4 | 111.1 |
| XXIV | Glucoisosacch-arinic Acid | NaOCl | 0.0 | 50.9 |
| XXV | Lactic Acid | NaOBr | 47.9 | 47.1 |
| XXVI | Lactic Acid | Na$_2$S$_2$O$_8$/Ag$^+$ | 76.0 | 148.2 |
| XXVII | Glycolic Acid | Na$_2$S$_2$O$_8$/Ag$^+$ | Trace | 109.1 |
| XXVIII | Glucoisosacch-arinic Acid | Na$_2$S$_2$O$_8$/Ag$^+$ | Trace | |

From the results shown in Table VI, Na$_2$S$_2$O$_8$ with AgClO$_4$ as a catalyst gave the best results, that is Example XXVI. In addition, Table VI shows the analysis of the DNPH derivatives of the aldehydes formed from the oxidation of the α-hydroxy acids using gas chromatography, (Column SP2100), or gas chromatography/mass spectrometry. The only major discrepancy occured in Example XV, that is the oxidation by NaOBr of lactic acid. Instead of forming acetaldehyde, only the formaldehyde derivative was detected. The results shown in Table VI further indicate that the conversion of saccharinic acids to lactic acid will enhance the formation of acetaldehyde during use of the present invention. On the other hand, it was also shown that the saccharinic acids are cleaved by the indicated oxidants into formaldehyde, acetaldehyde and proprionaldehyde. The major solution product was formic acid. The volatile aldehydes produced by these reactions were compatible with the overall process of the present invention.

Alternatively, the purified stream of hydroxy acids could be electrolyzed directly on anodes (e.g., platinum, dimensionally stable anodes coated with titanium or iridium metal, and a variety of other electrode materials). Electrolysis conditions such as constant current (100–200 mA/cm$^2$) at temperatures in the 50°–90° C. can be used in divided cells. For instance, a non-optimized cell yield of about 50% of acetaldehydes were obtained in alkaline solutions.

As can be seen from the above, a novel process has been provided whereby polyfunctional carboxylic acids may be readily decarboxylated to form their corresponding aldehydes which may subsequently be converted to useful end products such as peracids of lower carboxylic acids. Moreover, this process may be applied to various solution streams resulting from biomass processing systems which contain high concentrations of hydroxy acids. As has been seen from the above, these hydroxy acids are oftentimes merely burned off and lost during the process of recycling inorganic compounds used during wood pulping processes. By applying the concept of the present invention to solution streams derived from such processes, the hydroxy acids may be diverted and then subsequently converted to extremely useful substances for the wood pulping processes, such as peracids without affecting the normal flow of the pulping process itself, i.e. chemical recovery. In the preferred form, lactic acid, which is present in substantial amounts in black liquor solutions resulting from certain wood pulping processes, can be readily converted to peracetic acid, and this chlorinefree bleaching agent may be redirected and reused within the same pulping industry. Thus, application of the present invention may result in substantial economic savings due to the generation of useful products from biomass processing system by-products which are normally wasted.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to within the scope of the invention as defined by the claims which follow.

The embodiments of the invention in which an exclusive property or privilege is claimed are defined as follows:

1. In a wood pulp processing system of the type producing both pulp and a stream of lactic acid-containing black liquor solution, the processor for production of peracid bleaching agents from hydroxy acid contained in the black liquor solution, comprising:

adjusting the pH of said black liquor solution to the range of about 8-9 by exposing the solution to $CO_2$ carbon dioxide to form an alkaline precipitate;

separating solids from the black liquor solution to produce a residual solution containing lower aliphatic hydroxy acids selected from the group consisting of lactic acid, glycolic acid, 2-hydroxybutanoic acid, xyloisosaccharinic acid, and glucoisosaccharinic acid;

decarboxylating said lower aliphatic hydroxy acids to corresponding gaseous aliphatic aldehydes by admixing a powdered semiconductor with said residual solution to form a slurry, said semiconductor being selected from the group consisting of doped n-$TiO_2$, both platinized and unplatinized, n-$WO_3$, a-$Fe_2O_3$ and other insoluble semiconductors having bandgaps equal to or higher than a-$Fe_2O_3$, and then irradiating said slurry by a means for causing photoelectro-chemical reaction at the site of the semiconductor material resulting in decarboxylation of the carboxylic acid and produuction of $CO_2$ and corresponding aldehydes;

removing said gaseous aldehydes from the residual solution by sweeping gas flow as soon as they are generated to prevent further oxidation to carboxylic acids;

reacting said gaseous aldehydes with oxygen to form corresponding peracids; and applying said peracids as bleaching agents to said pulp produced in the pulp processing system.

2. The process as described in claim 1, further comprising:

cooking said black liquor solution or residual solution in the presence of oxygen for a time and at a temperature sufficient to form lactic acid from other hydroxy acids of the cooked solution, wherein said cooking step is performed prior to the step of decarboxylating the hydroxy acids.

3. The process as described in claim 2, wherein said cooking step is performed at a temperature in the range 150°-200° C. for a time from approximately 2-4 hours.

4. The process as described in claim 1, wherein said step of separating solids is performed by filtering any alkaline lignin components and ultrafiltering other residual components so as to separate said lower aliphatic hydroxy acids from higher hydroxy acids.

5. The process as described in claim 1, wherein said step of separating solids is performed by filtering any alkaline lignin components and membrane separating other residual components so as to separate said lower aliphatic hydroxy acids from higher hydroxy acids.

6. The process as described in claim 1, wherein said step of separating solids is performed by filtering any alkaline lignin components and then acidifying said solution to a pH of about 3-4 to precipitate any remaining alkaline components so as to leave a solution having predominently said lower aliphatic hydroxy acids.

* * * * *